(12) United States Patent
Tanaka et al.

(10) Patent No.: US 10,695,110 B2
(45) Date of Patent: Jun. 30, 2020

(54) INTERNAL FIXATOR FOR BONE FRACTURE

(71) Applicants: Sakae Tanaka, Tokyo (JP); Takehiro Matsubara, Tokyo (JP); Ikufumi Yamada, Kyoto (JP)

(72) Inventors: Sakae Tanaka, Tokyo (JP); Takehiro Matsubara, Tokyo (JP); Ikufumi Yamada, Kyoto (JP)

( * ) Notice: Subject to any disclaimer, the term of this patent is extended or adjusted under 35 U.S.C. 154(b) by 0 days.

(21) Appl. No.: 16/095,852

(22) PCT Filed: Apr. 25, 2017

(86) PCT No.: PCT/JP2017/016396
§ 371 (c)(1),
(2) Date: Oct. 23, 2018

(87) PCT Pub. No.: WO2017/188261
PCT Pub. Date: Nov. 2, 2017

(65) Prior Publication Data
US 2019/0336186 A1 Nov. 7, 2019

(30) Foreign Application Priority Data

Apr. 25, 2016 (JP) .................. 2016-099968
Jun. 29, 2016 (JP) .................. 2016-140860

(51) Int. Cl.
*A61B 17/74* (2006.01)
*A61B 17/72* (2006.01)

(52) U.S. Cl.
CPC ........ *A61B 17/744* (2013.01); *A61B 17/7233* (2013.01); *A61B 17/7283* (2013.01); *A61B 17/748* (2013.01)

(58) Field of Classification Search
CPC .............. A61B 17/744; A61B 17/7233; A61B 17/7241; A61B 17/725; A61B 17/7283; A61B 17/748
See application file for complete search history.

(56) References Cited

U.S. PATENT DOCUMENTS

| 4,135,507 A | 1/1979 | Harris |
| 5,429,640 A | 7/1995 | Shuler et al. |

(Continued)

FOREIGN PATENT DOCUMENTS

| JP | 2004-305671 A | 11/2004 |
| JP | 2009-112594 A | 5/2009 |
| JP | 2012-531955 A | 12/2012 |

*Primary Examiner* — Ellen C Hammond
(74) *Attorney, Agent, or Firm* — Carrier Blackman & Associates, P.C.; William D. Blackman; Joseph P. Carrier

(57) ABSTRACT

A bone fracture internal fixator for repairing a bone fracture of a femoral neck that allows load to be applied to the associated bone parts evenly, and increases the connecting strength between the femoral head and femoral shaft while minimizing the risk of the femoral head being torn apart by the inner connecting member by increasing the diameter of the inner fixing member. The central axial line of the femoral head is offset from the central axial line of the intramedullary nail placed in the medullary cavity of the femoral shaft. In order to bring the inner fixing member such as a lag screw configured to be inserted through the femoral neck close to the central axial line of the femoral neck, the central axial line of the through hole for receiving the inner fixing member is offset from the central axial line of the intramedullary nail.

6 Claims, 18 Drawing Sheets

(56) References Cited

U.S. PATENT DOCUMENTS

| | | | | |
|---|---|---|---|---|
| 6,126,661 | A * | 10/2000 | Faccioli | A61B 17/72 606/64 |
| 7,488,320 | B2 * | 2/2009 | Middleton | A61B 17/0401 606/323 |
| 8,834,469 | B2 * | 9/2014 | Watanabe | A61B 17/7225 606/64 |
| 2010/0179551 | A1 | 7/2010 | Keller et al. | |
| 2012/0143192 | A1 | 6/2012 | Watanabe et al. | |

* cited by examiner

PRIOR ART

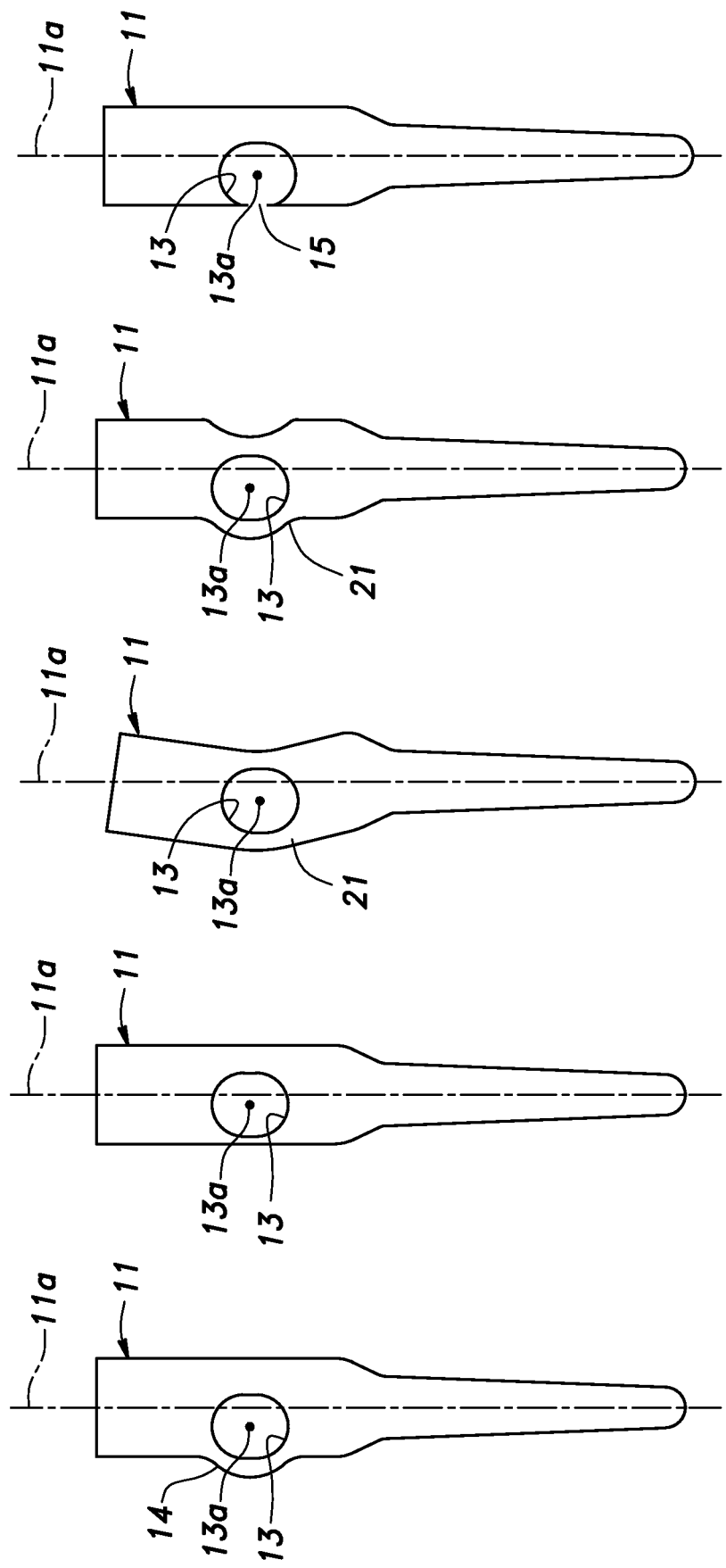

INTERNAL FIXATOR FOR BONE FRACTURE

TECHNICAL FIELD

The present disclosure relates to an internal fixator for stabilizing a bone fracture in the field of orthopedic surgery, and, in particular, to a bone fracture internal fixator for repairing a femoral neck fracture.

BACKGROUND ART

As shown in FIG. 1, a bone fracture 3 occurs to a femoral neck 2 that defines a boundary between a femoral head 4 and a femoral shaft 5. A greater trochanter 6 and a lesser trochanter 7 are located on the side of the femoral shaft 5. As shown in FIGS. 2 to 4, a conventional internal fixator 101 for repairing a femoral neck fracture includes an intramedullary nail 102 passed into a medullary cavity of a femoral shaft 5, and a lag screw 103 that connects a femoral head 4 to the femoral shaft 5 (see Patent Document 1, for example). The lag screw 103 is passed into a through hole 104 formed in the intramedullary nail 102 from the threaded front end thereof so that the front end thereof is fixed in the femoral head 4, and the rear end thereof is supported in the through hole 104.

PRIOR ART DOCUMENT(S)

Patent Document(s)

Patent Document 1: JP2009-112594A

SUMMARY OF THE INVENTION

Task to be Accomplished by the Invention

However, such an internal fixator 101 has the following problems.

The first problem is that since the diameter of the intramedullary nail 102 is limited by the size of the medullary cavity of the femoral shaft 5, the diameter of the lag screw 103 inserted through the through hole 104 of the intramedullary nail 102 is also limited in a corresponding manner.

The second problem is that the diameter of the lag screw 103 is limited because the lag screw 103 cannot be inserted into the central axial line 2a of the femoral neck 2 as will be discussed in the following. In the actual procedure, the through hole 104 of the intramedullary nail 102 is located in an upper part of the femoral shaft 5 corresponding to the position the lesser trochanter 7. As shown in FIG. 5, in cross sectional view, an offset 105 of about 4 mm is created between the central axial line 2a of the femoral neck 2 and the central axial line 102a of the intramedullary nail 102 owing to an anatomical attribute of this part. On the other hand, the through hole 104 of the conventional intramedullary nail 102 through which the lag screw 103 is passed is configured such that the central axial line 102a of the intramedullary nail 102 intersects with the central axial line 104a of the through hole 104. In the conventional procedure, as shown in FIGS. 6A-6B, a guide wire 106 is inserted into the femoral head 4 via the through hole 104 of the intramedullary nail 102 (FIG. 6A), and a bone hole is formed in the femoral head 4 with a cannulated drill (not shown in the drawings) by using the guide wire 106 as a guide so that the lag screw 103 may be inserted into the bone hole via the guide wire 106 (of FIG. 6B). As a result, the central axial line 103a of the lag screw 103 is offset from the central axial line 2a of the femoral neck 2 by a certain offset 105. If the offset 105 is 4 mm, for example, the central axial line 103a of the lag screw 103 is offset by 4 mm from the central axial line 2a of the femoral neck 2. The closer the central axial line 103a of the lag screw 103 is to the central axial line 102a of the femoral neck 2, the thicker the lag screw 103 can be. However, in reality, owing to such an offset 105, the thickness of the lag screw 103 is limited.

The third problem is that the load balance is not favorable. If the central axial line 103a of the lag screw 103 is offset from the central axial line 2a of the femoral neck 2 as discussed in conjunction with the second problem, the load that is applied to the internal fixator 101 due to a walking motion of the patient causes an uneven load to the associated bone parts. In particular, the loading at the fracture interface becomes uneven. This is undesirable in a situation where the patient performs walking exercises shortly after a bone repair operation has been performed.

The fourth problem is that the inner diameter of the through hole 104 is limited for the purpose of ensuring an adequate mechanical strength to the intramedullary nail 102, and this in turn limits the outer diameter of the lag screw 103.

Due to such problems, the diameter of the lag screw 103 cannot be increased so much as desired so that the fixing strength between the femoral head 4 and the femoral shaft 5, and the withdrawing resistance of the lag screw 103 are less than desired.

As shown in FIG. 7, at the time of walking, a load F directed in the direction indicated by the arrow acts on the femoral head 4 from the pelvis 8. At this time, a large part of the load F acts upon a front end part of the lag screw 103. This is inconvenient because the front end part of the lag screw 103 has a relatively small diameter. Therefore, when the patient starts walking exercise shortly after surgery, the bone fracture 3 may become so unstable that the patient may experience pain. It is also possible for the femoral head 4 to be torn apart by the lag screw 103, the bone fracture 3 to be dislocated as shown in FIG. 8.

In view of such problems of the prior art, a primary object of the present invention is to provide an internal fixator for repairing a bone fracture of a femoral neck that allows load to be applied to the associated bone parts evenly, and increases the connecting strength between the femoral head and the femoral shaft while minimizing the risk of the femoral head being torn apart by the internal fixator by at least partly increasing the diameter of the internal fixator (such as a lag screw).

Means for Accomplishing the Task

To achieve such an object, the present invention provides a bone fracture internal fixator (10, 30, 40, 70) for repairing a bone fracture of a femoral neck (2), comprising: an intramedullary nail (11, 31, 41, 71) configured to be passed into a medullary cavity of a femoral shaft (5) and provided with a through hole (13, 33, 43, 73) in an upper part thereof; and a rod-shaped inner fixing member (12, 32, 42, 72) including a shaft portion (17, 34, 45, 74) configured to be passed through the through hole and the femoral neck, and a front end portion (18, 35, 46, 75) configured to be pierced into a femoral head (4); wherein a central axial line of the front end portion of the inner fixing member is offset from a central axial line of the intramedullary nail toward a central axial line of the femoral neck.

Owing to this arrangement, the front end portion configured to be pierced into the femoral head comes close to the central axial line of the femoral neck so that the load from the pelvis can be supported in an evenly distributed manner. The diameter of the front end portion can be maximized so that the force for fixing the femoral head and the front end portion to each other, and the withdrawing resistance can be increased, and the risk of the femoral head being torn by the front end portion can be minimized.

In the bone fracture internal fixator (10, 30, 40, 70) according to a certain aspect of the present invention, a center of the through hole (13, 43, 73) is offset from the central axial line of the intramedullary nail (11, 41, 71), and the central axial line of the front end portion of the inner fixing member (12, 42, 72) coincides with a central axial line of the shaft portion.

Because the central axial line of the through hole is offset from the central axial line of the intramedullary nail, the inner fixing member may be configured to be extending linearly so that the shaft portion and the front end portion of the inner fixing member can be both increased in diameter. Therefore, the force for fixing the femoral head and the front end portion to each other, and the withdrawing resistance can be increased. Because not only the front end portion but also the shaft portion are brought close to the central axial line of the femoral neck, the load from the pelvis can be supported in an evenly distributed manner.

In the bone fracture internal fixator (30) according to another aspect of the present invention, the front end portion (35) and the shaft portion (34) consist of two separate parts that are connected to each other via a connecting structure, an outer diameter of at least a part of the front end portion being greater than an inner diameter of the through hole (33).

Because the front end portion and the shaft portion consist of two separate parts, when installing the bone fracture internal fixator in a patient, the front end portion is not required to be passed through the through hole so that the outer diameter of the front end portion may be greater than the inner diameter of the through hole. Therefore, the diameter of the front end portion may be increased so that the force for fixing the femoral head and the front end portion to each other, and the withdrawing resistance can be increased, and the risk of the femoral head being torn by the front end portion can be minimized.

In the bone fracture internal fixator according to yet another aspect of the present invention, a lateral dimension of a part (14, 44) of the intramedullary nail defining the through hole as measured in a direction orthogonal to an extending direction of the through hole is greater than parts of the intramedullary nail above and below the through hole.

Since the through hole is formed in a widened portion of the intramedullary nail, the inner diameter of the through hole can be increased so that the diameter of the inner fixing member or the offset of the central axial line of the through hole from the central axial line of the intramedullary nail can be increased.

In the bone fracture internal fixator according to yet another aspect of the present invention, a rear end part (51) of the shaft portion is narrowed.

Thereby, the bone hole formed in the femur for inserting the inner fixing member can be quickly restored so that the strength of the bone can be recovered in a relatively short period of time.

In the bone fracture internal fixator according to yet another aspect of the present invention, one of the intramedullary nail and the inner fixing member is formed with a groove (56) extending along an extending direction of the through hole, and another of the intramedullary nail and the inner fixing member is formed with a projection (61) engaged by the groove.

Thereby, the rotation of the inner fixing member around the axial line thereof can be prevented so that the rotation of the femoral head relative to the femoral shaft along the bone fracture can be prevented.

In the bone fracture internal fixator according to yet another aspect of the present invention, the shaft portion is formed as a tubular member internally defining a fluid passage (47), and a surface of the front end portion is formed with an injection hole (48) communicating with the fluid passage.

This arrangement allows bone cement, an osteogenic agent, artificial bone or the like to be injected into a space defined between the front end portion and the femoral head via the fluid passage and the injection hole after the bone fracture internal fixator is installed in the femur. Once the injected substance has spread around the front end portion, and has solidified, the front end portion can be firmly secured to the femoral head, and the load transmitted from the femoral head to the front end portion can be evenly distributed so that the load supporting capability of the front end portion can be enhanced, and the risk of the femoral head being torn apart by the front end portion can be reduced.

In the bone fracture internal fixator according to yet another aspect of the present invention, the intramedullary nail is formed with a female threaded hole (53) extending across a lower part of the intramedullary nail.

By fastening a laterally extending screw into the female threaded hole extending across the lower part of the intramedullary nail, the intramedullary nail can be firmly secured to the femoral shaft.

In the bone fracture internal fixator according to yet another aspect of the present invention, a lower part of the intramedullary nail is provided with a curved part (26) conforming to an extending direction of the medullary cavity of the femoral shaft.

Thereby, the intramedullary nail can be placed in the medullary cavity in an undeviating manner.

Effects of the Invention

According to the bone fracture internal fixator for repairing a femoral neck fracture of the present invention, the load from the pelvis can be supported in an evenly distributed manner Also, by at least partly thickening the inner fixing member (lag screw etc.), the connection between the inner fixing member and the femur can be strengthened, and the risk of the femoral head being torn apart by the inner fixing member can be reduced.

BRIEF DESCRIPTION OF THE DRAWING(S)

FIGS. 6A-6B are perspective views showing a positioning of a lag screw; wherein FIG. 6A shows a guide wire inserted into a femoral head via a through hole of an intramedullary nail, and FIG. 6B shows a lag screw inserted into the bone hole via the guide wire;

Figure 12C:
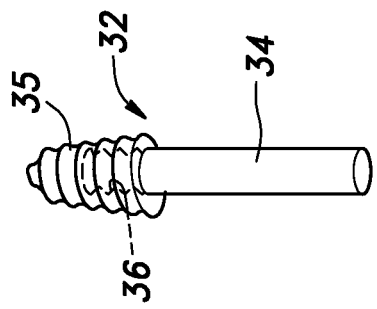
Figure 12B:
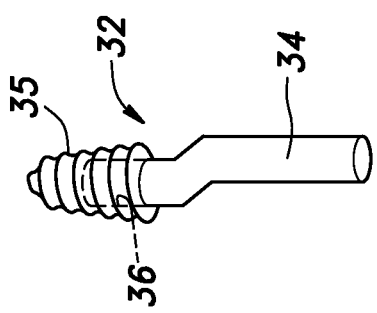
Figure 12A:
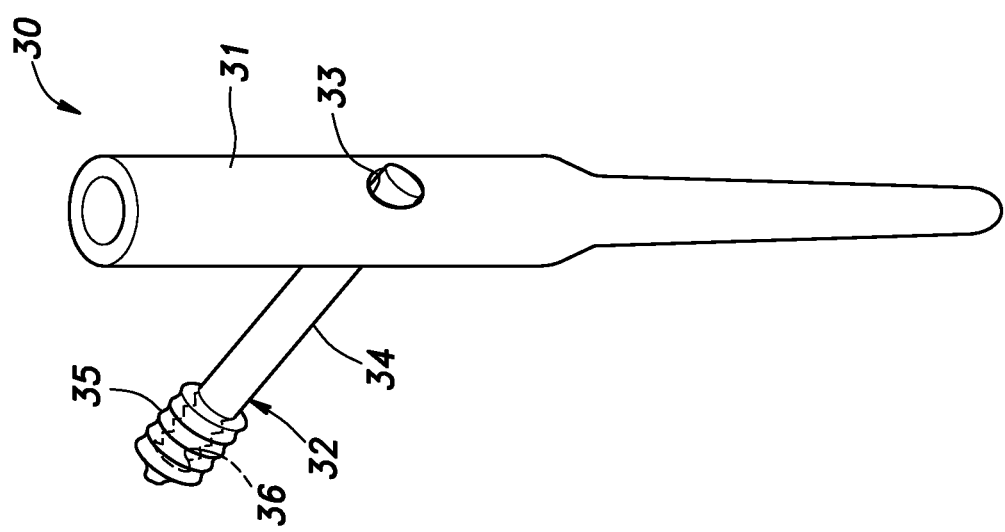
Figure 13:
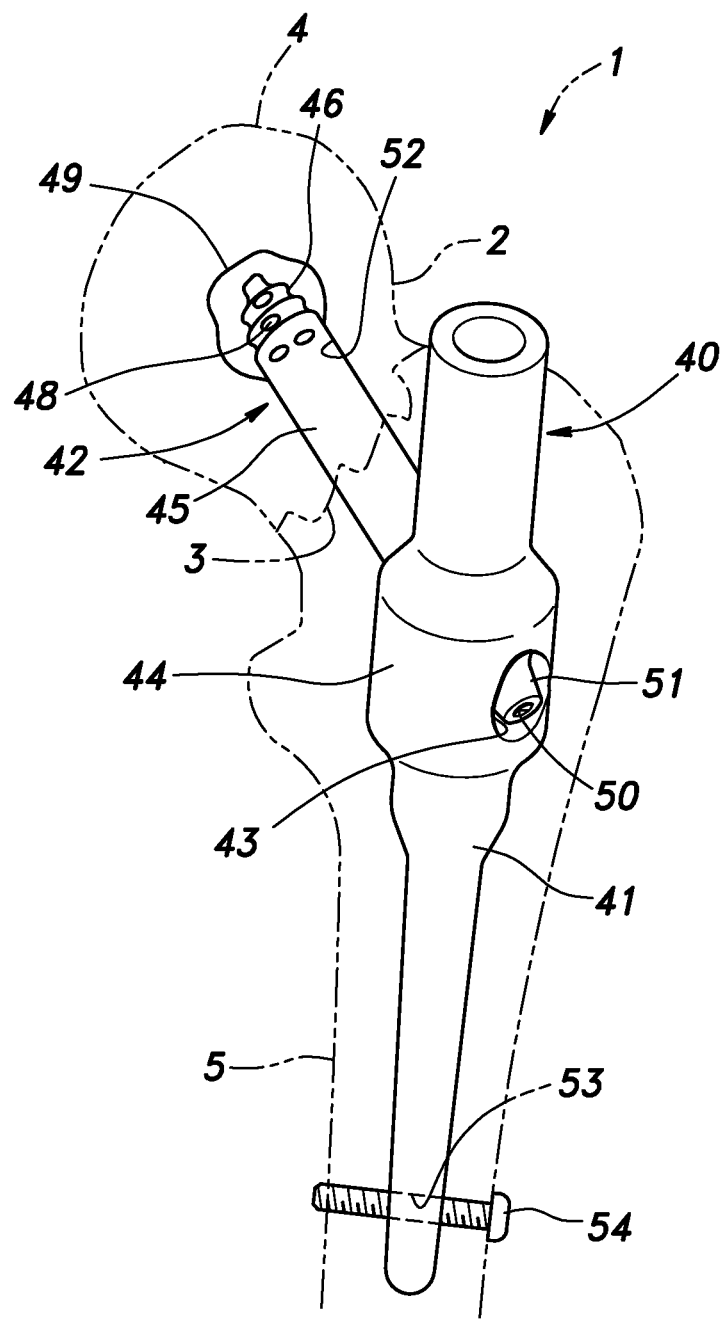
Figure 14:
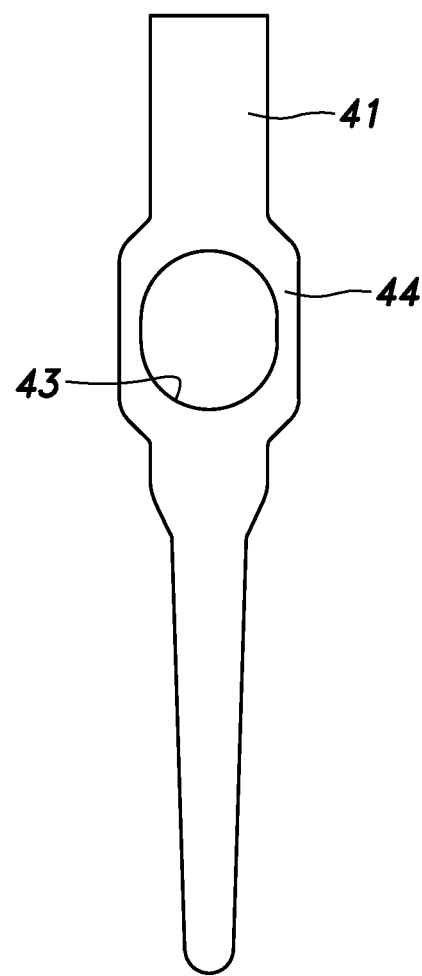
Figure 15:
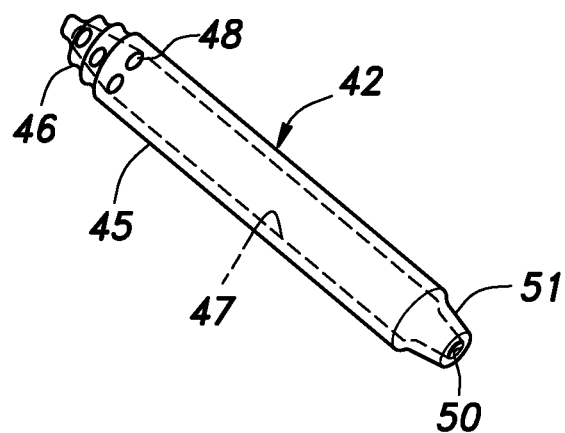
Figure 16A:
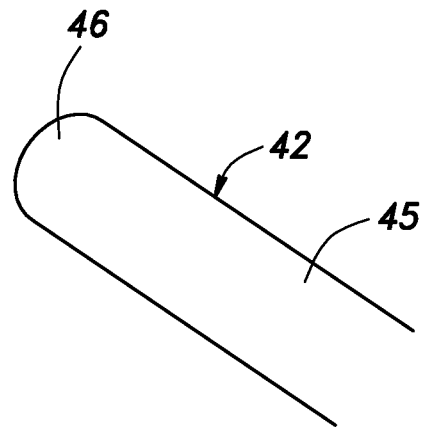
Figure 16B:
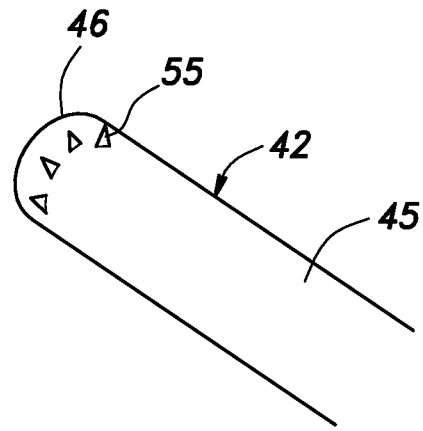
Figure 17C:
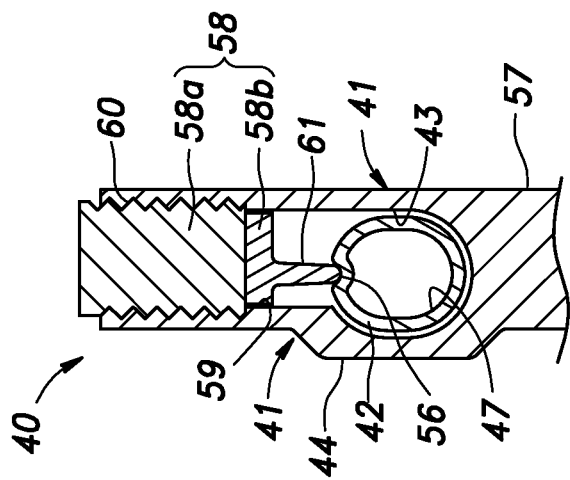
Figure 17B:
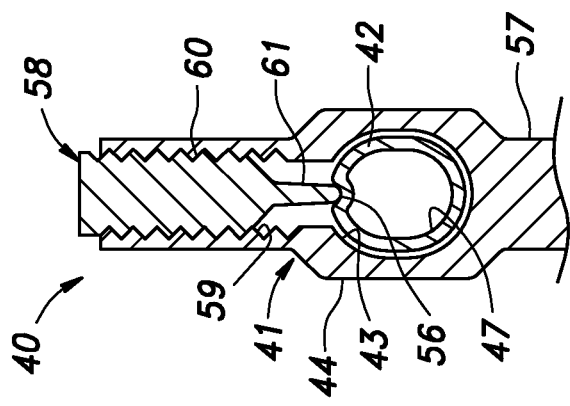
Figure 17A:
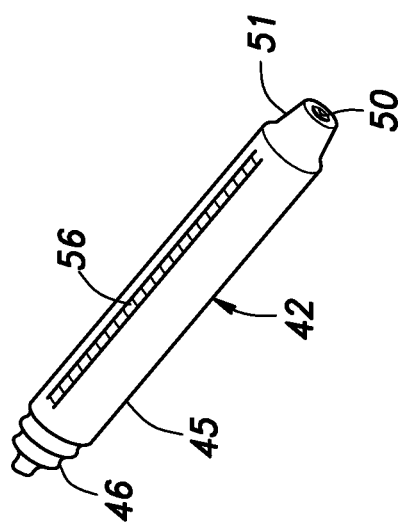
Figure 18C:
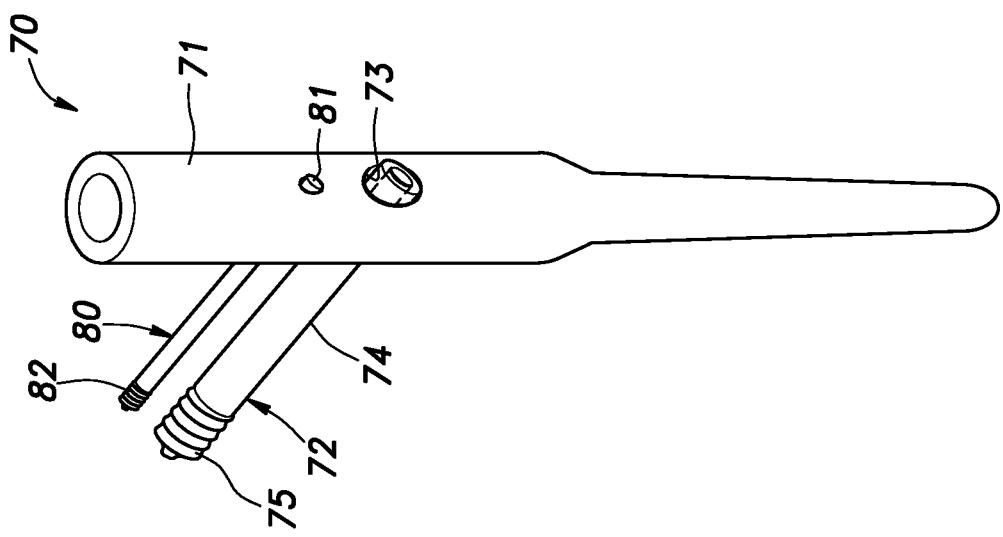
Figure 18B:
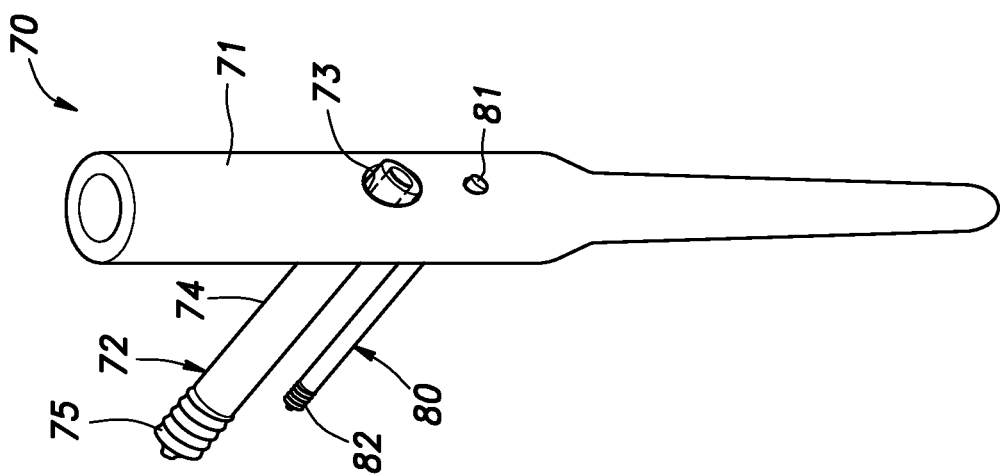
Figure 18A:
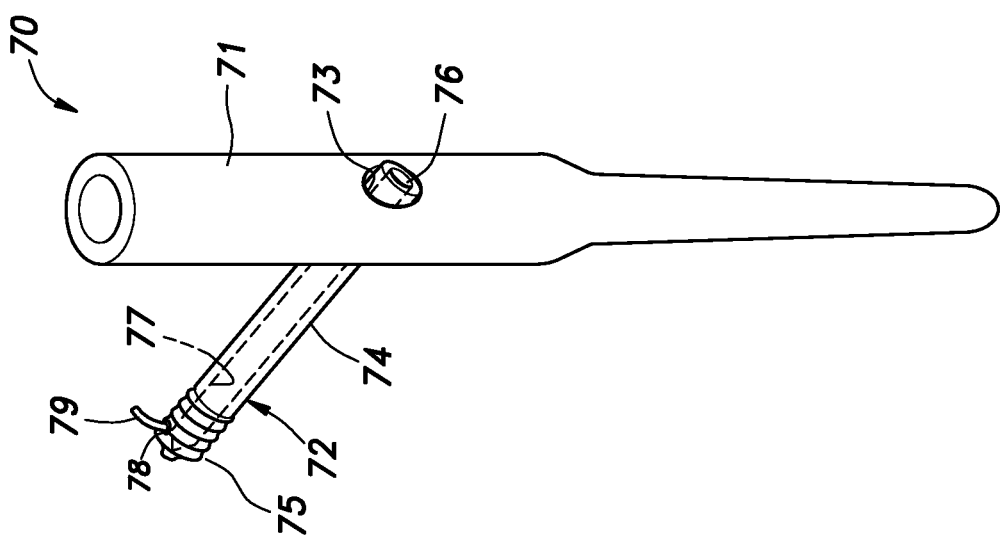

FIGS. 11A-11E show side views of intramedullary nails of the first embodiment and modifications thereof, wherein FIG. 11A shows a first embodiment, FIG. 11B shows a modified embodiment 1, FIG. 11C shows a modified embodiment 2, FIG. 11D shows a modified embodiment 3, and FIG. 11E shows a modified embodiment 4;

FIGS. 12A-12C show perspective views of a second embodiment and modifications thereof, wherein FIG. 12A shows a bone fracture internal fixator, FIG. 12B shows a modification of the an inner fixing member, and FIG. 12C shows another modification of the internal fixing member;

FIG. 13 is a perspective view of a bone fracture internal fixator according to a third embodiment;

FIG. 14 is a side view of an intramedullary nail of the third embodiment;

FIG. 15 is a perspective view of an inner fixing member of the third embodiment;

FIGS. 16A-16B show perspective views of front end portions of inner fixing members of modifications of the third embodiment, wherein FIG. 16A shows a modified embodiment; and FIG. 16B shows another modified embodiment);

FIGS. 17A-17C show engagement structures provided between the intramedullary nail and the inner fixing member given as modifications of the third embodiment, wherein FIG. 17A is a perspective view of the inner fixing member, FIG. 17B is a sectional view showing a state of engagement between the intramedullary nail and the inner fixing member, and FIG. 17C is a sectional view showing a state in which the central axes of the intramedullary nail and the inner fixing member are offset from each other similarly as in the first embodiment); and FIGS. 18A-18C show perspective views of bone fracture internal fixators according to a fourth embodiment and modifications thereof, wherein FIG. 18A is an embodiment using a projection, FIG. 18B is an embodiment using an auxiliary screw, and FIG. 18C is another embodiment using an auxiliary screw).

DESCRIPTION OF THE PREFERRED EMBODIMENT(S)

Preferred embodiments of the present invention are described in the following with reference to the appended drawings.

First Embodiment

Figure 9:
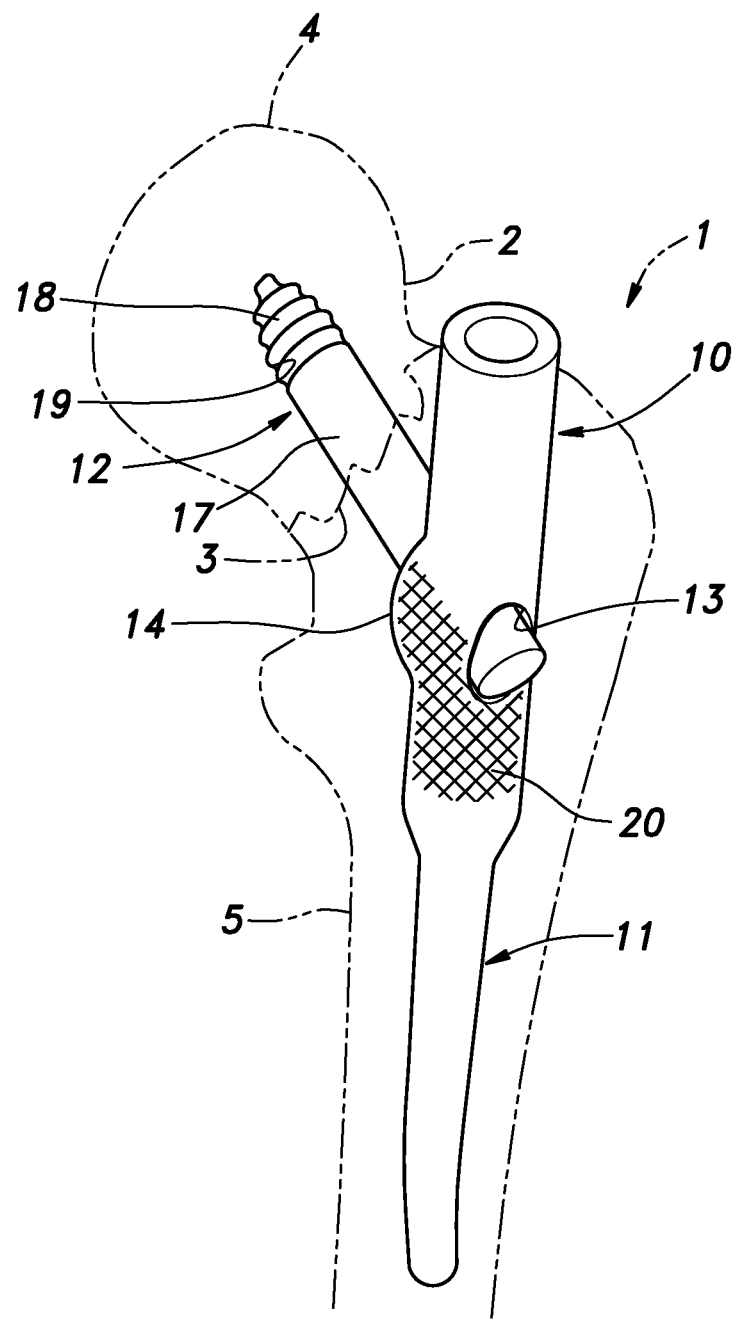
FIG. 9 is a perspective view showing a use state of a bone fracture internal fixator for repairing a femoral neck fracture according to a first embodiment of the present invention.
Figure 10:
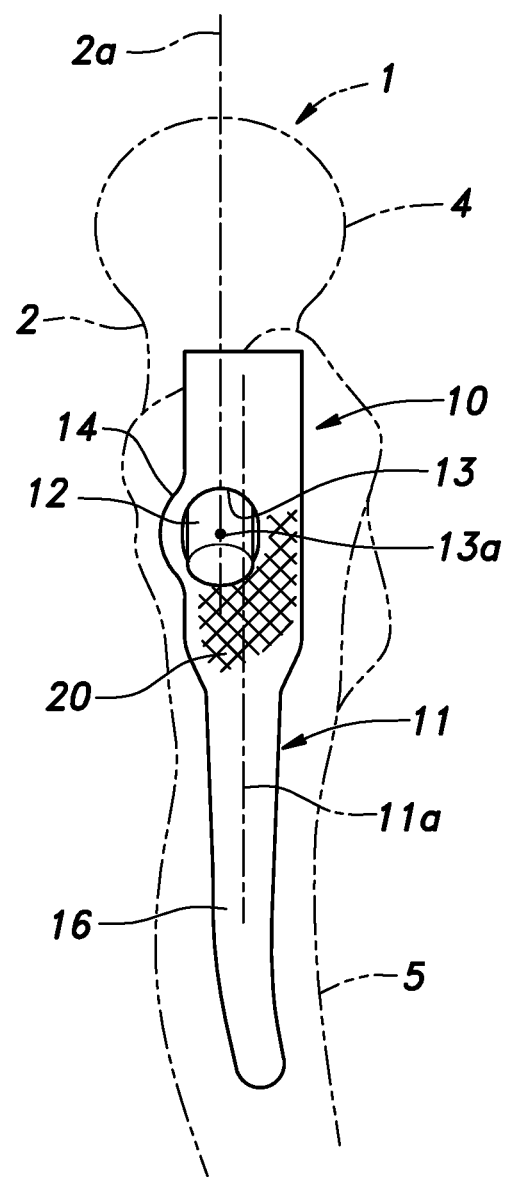
FIG. 10 is a side view of the bone fracture internal fixator of the first embodiment.

FIGS. 9 and 10 show a bone fracture internal fixator 10 for repairing a femoral neck fracture according to a first embodiment. The bone fracture internal fixator 10 includes an intramedullary nail 11 configured to be placed in the medullary cavity of a femoral shaft 5, and a rod-shaped inner fixing member 12 configured to be connected between a femoral head 4 and the femoral shaft 5.

As shown in FIG. 11A, the intramedullary nail 11 is formed with a through hole 13 through which the inner fixing member 12 may be passed, and the central axial line 13a of the through hole 13 is laterally offset from the central axial line 11a of the intramedullary nail 11. The through hole 13 is formed in a widened portion 14 of the intramedullary nail 11, and the width of the widened portion 14 as measured in a direction orthogonal to the extending direction of the through hole 13 is greater than the widths of the parts of the intramedullary nail 11 above and below the widened portion 14.

FIGS. 11B-11E show modified embodiments of the intramedullary nail 11. In the modified embodiment shown in FIG. 11B, no widened portion 14 is provided, and the central axial line 13a of the through hole 13 is simply offset from the central axial line 11a of the intramedullary nail 11 in the width direction. In the modified embodiment shown in FIG. 11C, instead of providing a widened portion 14, an upper part 21 of the intramedullary nail 11 is generally curved so that the central axial line 13a of the through hole 13 is offset from the central axial line 11a of the intramedullary nail 11 (the extension line of the central axial line of the part of the intramedullary nail 11 extending linearly along the length of the medullary cavity of the femoral shaft 5). In the modified embodiment shown in FIG. 11D, instead of providing a widened portion 14, an upper part 21 of the intramedullary nail 11 is locally curved, or a part of the intramedullary nail 11 defining the through hole 13 is locally curved so that the central axial line 13a of the through hole 13 is offset from the central axial line 11a of the intramedullary nail 11 (the extension line of the central axial line of the part of the intramedullary nail 11 extending linearly along the length of the medullary cavity of the femoral shaft 5). In the modified embodiment shown in FIG. 11E, the central axial line 13a of the through hole 13 is simply offset from the central axial line 21a of the intramedullary nail 11 in the width direction so that the through hole 13 is not entirely surrounded by a wall, and a cutout 15 is formed in a part of the wall.

A coating 20 made of such material as hydroxyapatite may be applied to the surface of the inner fixing member 12 or the intramedullary nail 11 so that the bone fracture internal fixator 10 may acquire a supporting force against a longitudinal load. Instead of applying such a coating 20, an irregular surface feature or a porous structure may be provided on the surface. Further, as shown in FIG. 10, the lower end part of the intramedullary nail 11 may be provided with a curved part 16 corresponding to the forward curving of the femoral shaft 5 in order to prevent the intramedullary nail 11 from deviating sideways in the medullary cavity.

As shown in FIG. 9, the inner fixing member 12 is provided with a shaft portion 17 configured to be inserted through the through hole 13 and the femoral neck 2, and a front end portion 18 configured to be inserted or pierced into the femoral head 4. The inner fixing member 12 is a rod-like member extending linearly, and is formed as a lag screw having a male thread formed in the front end portion 18. By threading the front end portion 18 into the femoral head 4, the inner fixing member 12 is fixedly secured to the femoral head 4. Further, the rear end part of the shaft portion 17 is supported by the intramedullary nail 11 fixed to the femoral shaft 5 by being tightly or loosely fitted in the through hole 13. If desired, the outer circumferential surface of the rear end part of the shaft portion 17 may be formed with a male thread while the inner circumferential surface of the through hole 13 is formed with a corresponding female thread so that the two parts may be fastened to each other.

Figure 6A:
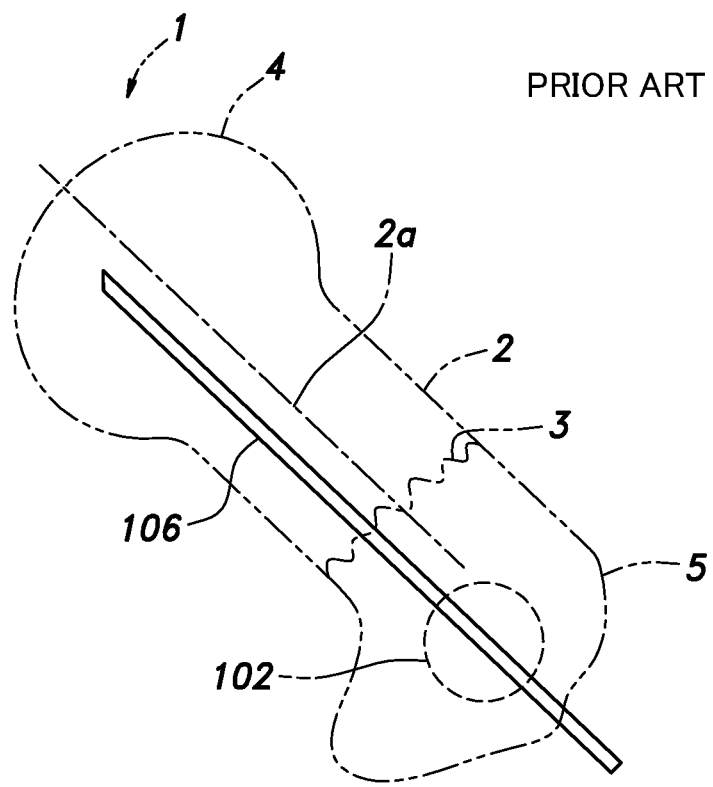
Figure 6B:
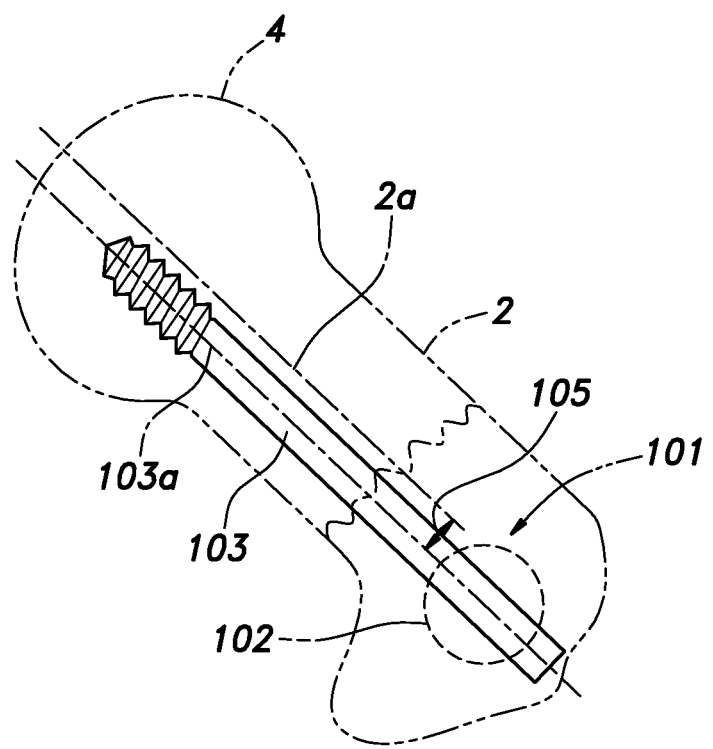
Figure 7:
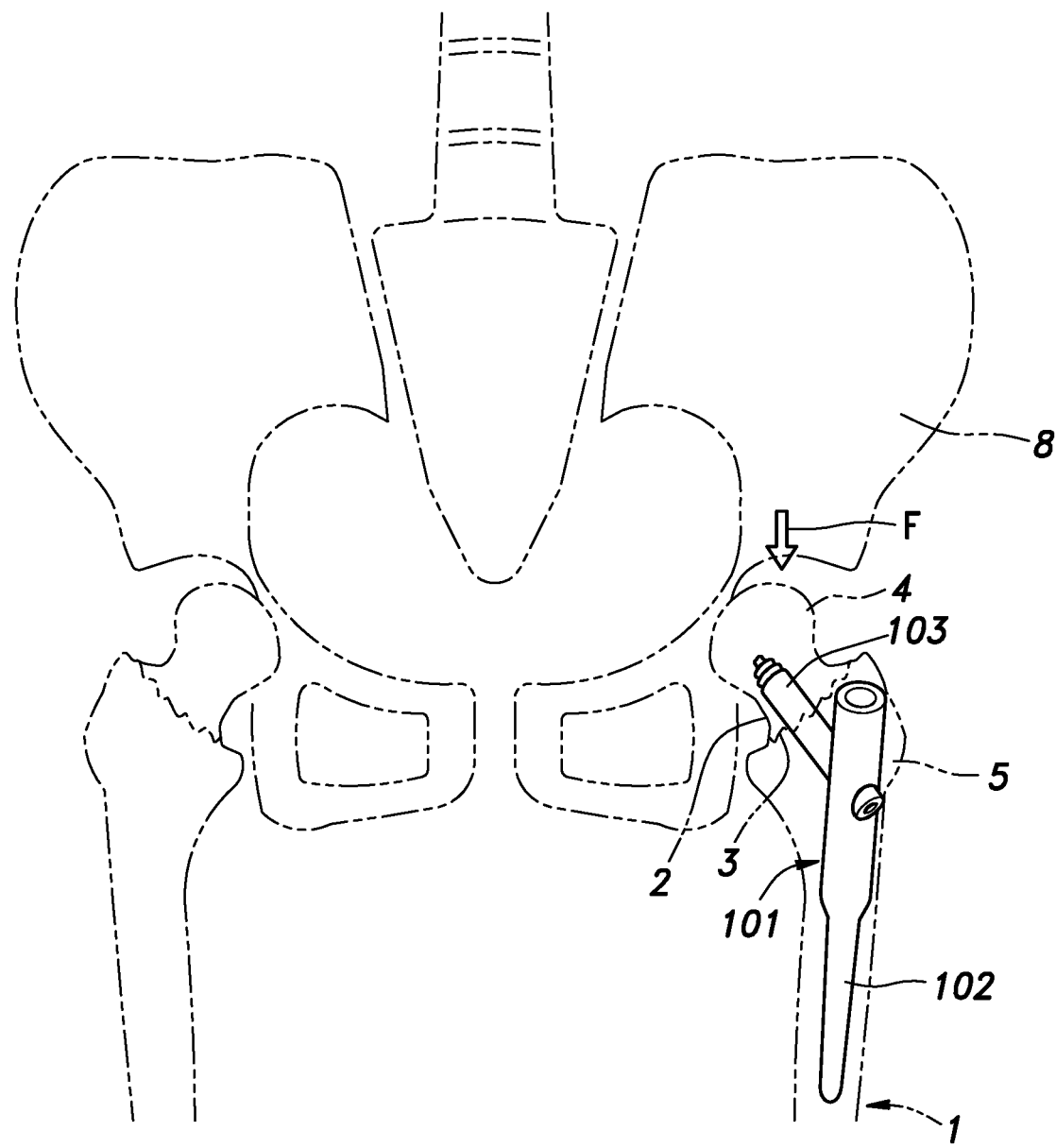
FIG. 7 is a perspective view showing a use state of the conventional bone fracture internal fixator for repairing a femoral neck fracture.
Figure 8:
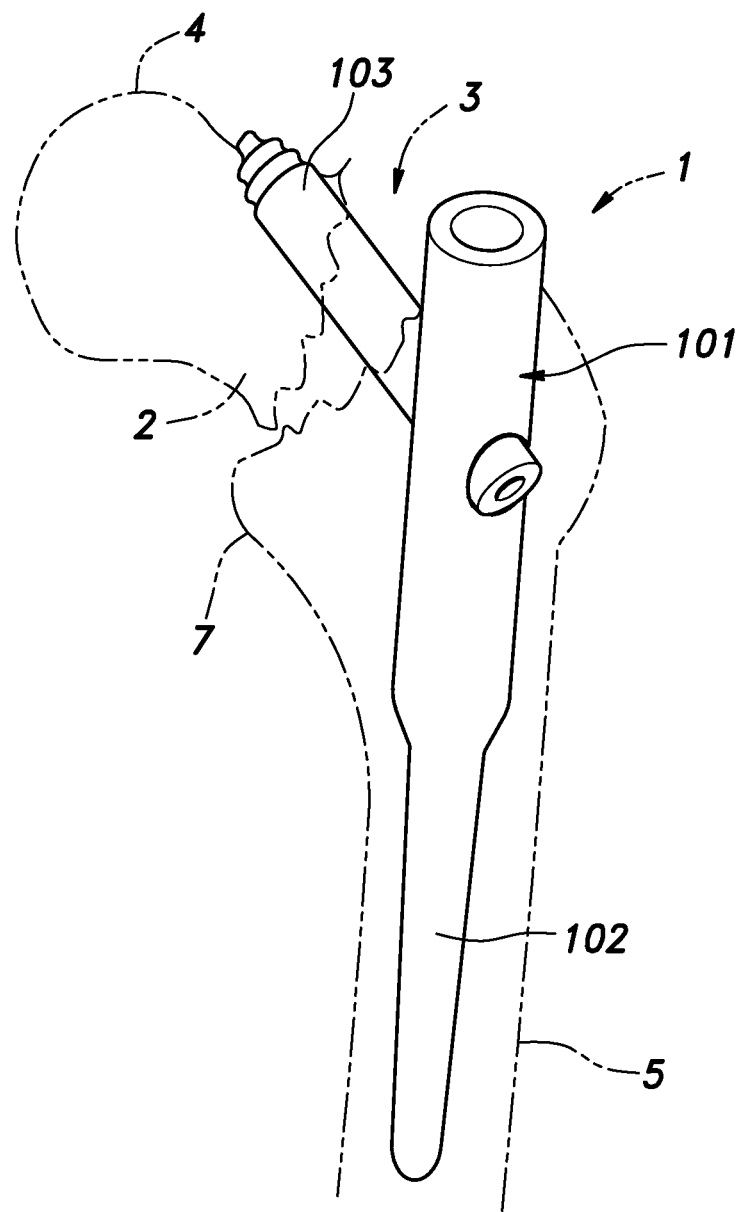
FIG. 8 is a perspective view showing a use state of the conventional bone fracture internal fixator for repairing a femoral neck fracture.

The procedure for installing the bone fracture internal fixator 10 is described in the following. First of all, the intramedullary nail 11 is inserted into the medullary cavity of the femoral shaft 5. At this time, the intramedullary nail 11 is arranged so that the direction of the offset of the central axial line 13a of the through hole 13 from the central axial line 21a of the intramedullary nail 11 is directed toward the central axial line 2a of the femoral neck 2. Next, a guide wire 106 (see FIG. 6) is inserted into the femoral head 4 through the through hole 13, and by using the guide wire 106 as a guide, a cannulated drill is inserted into the femoral head 4 to form a bone hole 19 in a part of the femoral head 4 in which the inner fixing member 12 is to be inserted. Then, the inner fixing member 12 is inserted into the through hole 13 and the bone hole 19 with the front end portion 18 first. At this time, by turning the inner fixing member 12 around the axial line thereof to cause a self-tapping action of the inner fixing member 12, the front end portion 18 is firmly fastened to the femoral head 4. By installing the bone fracture internal fixator 10 in this manner, the bone fracture 3 is secured.

In the case of the bone fracture internal fixator 10 of the first embodiment, since the central axial line 13a of the through hole 13 is offset from the central axial line 11a of the intramedullary nail 11 in the lateral direction, the inner fixing member 12 can be inserted in a part of the femoral neck 2 close to the central axial line 2a thereof so that the load balance is improved. As a result, the pain in the bone fracture 3 can be reduced as compared with the conventional device. Since the repaired part can tolerate a loading thereto from an early stage of recovery, progress of rehabilitation can be accelerated.

According to the bone fracture internal fixator 10 of the first embodiment, since the central axial line 13a of the through hole 13 is offset from the central axial line 11a of the intramedullary nail 11 in the lateral direction, the diameter of the inner fixing member 12 can be increased more than was possible by the prior art. Suppose that the width (diameter) of the medullary cavity of the femoral neck 2 is 18 mm and the central axial line 2a of the femoral neck 2 is deviated from the central axial line 11a of the intramedullary nail 11 by 4 mm. According to the prior art, in order to ensure a distance of 1 mm or more between the outer circumferential surface of the inner fixing member 12 and the outer surface of the femoral neck 2 to avoid any contact between the inner fixing member 12 and the cortical bone, the diameter of the lag screw (inner fixing member 12) must be 8 mm or less. However, according to the bone fracture internal fixator 10 of the first embodiment, the deviation can be reduced to 0 mm, and in such a case, the diameter of the inner fixing member 12 may be up to 16 mm in theory. By increasing the thickness of the inner fixing member 12 in this manner, the securing force and the withdrawing resistance force that are afforded to the inner fixing member 12 in relation to the femoral head 4 and the femoral shaft 5 can be substantially increased. Furthermore, the load acting between the front end portion 18 of the inner fixing member 12 and the femoral head 4 can be widely distributed so that the risk of the femoral head 4 being torn apart can be reduced.

Second Embodiment

FIG. 12A shows a bone fracture internal fixator 30 according to a second embodiment. Similarly to the first embodiment, the bone fracture internal fixator 30 includes an intramedullary nail 31 configured to be placed in the medullary cavity of the femoral shaft 5, and a rod-like inner fixing member 32 configured to be connected between the femoral head 4 and the femoral shaft 5. In particular, the structure of the inner fixing member 32 differs from that of the inner fixing member 12 of the first embodiment. The parts corresponding to those of the first embodiment may be omitted in the following disclosure.

The intramedullary nail 31 is constructed in a similar manner as the conventional one. More specifically, the central axial line of the through hole 33 crosses the central axial line of the intramedullary nail 31, instead of being offset therefrom.

Figure 1:
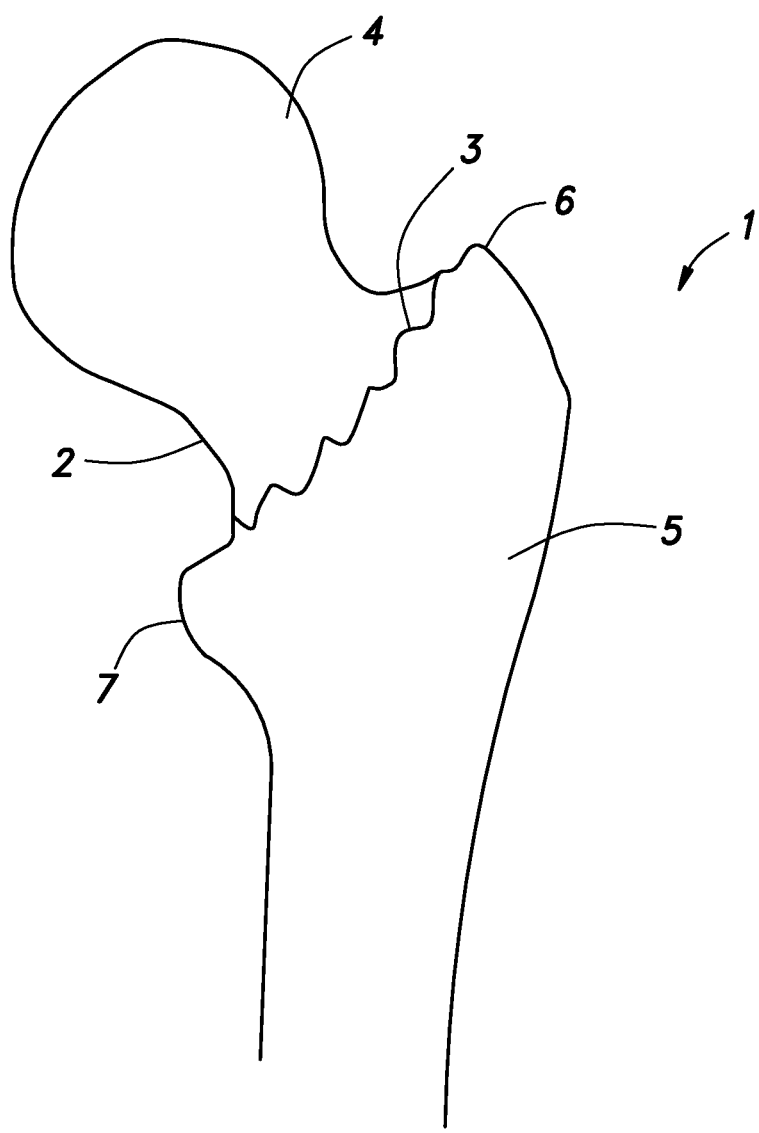
FIG. 1 is a perspective view showing a femoral neck fracture.
Figure 2:
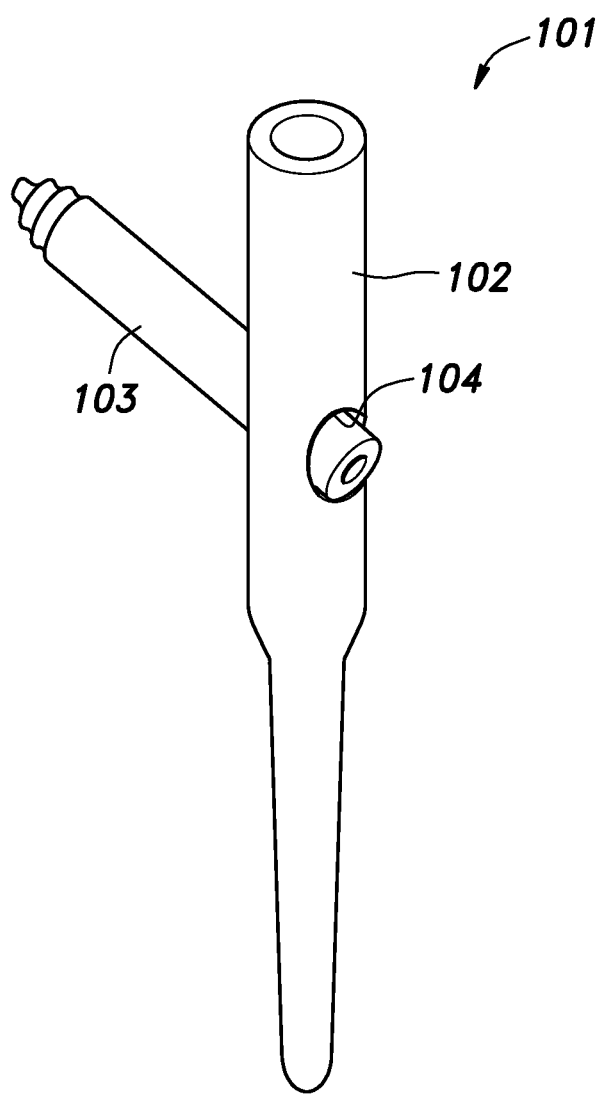
FIG. 2 is a perspective view showing a conventional bone fracture internal fixator for repairing a femoral neck fracture.
Figure 3:
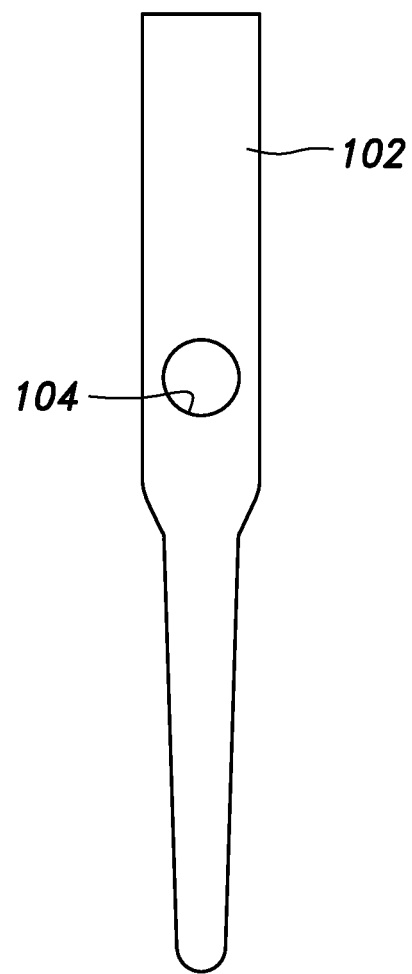
FIG. 3 is a side view showing a conventional intramedullary nail.
Figure 4:
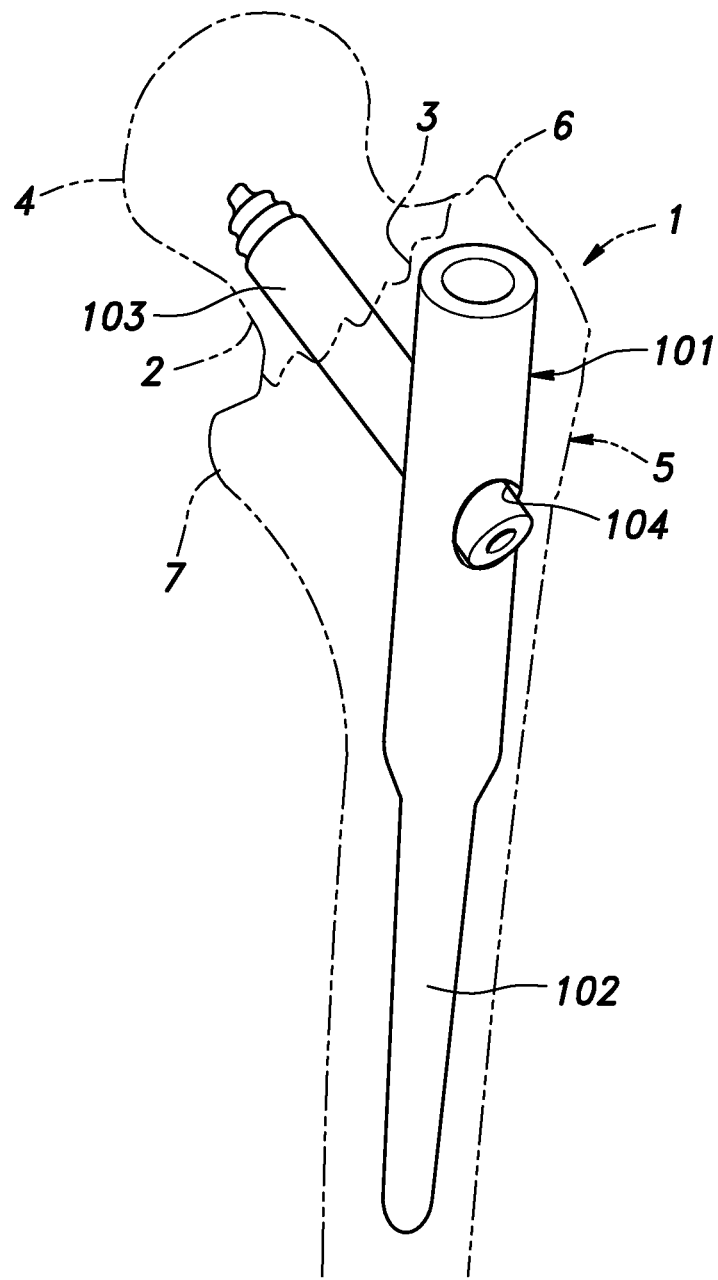
FIG. 4 is a perspective view showing a use state of the conventional bone fracture internal fixator for repairing a femoral neck fracture.
Figure 5:
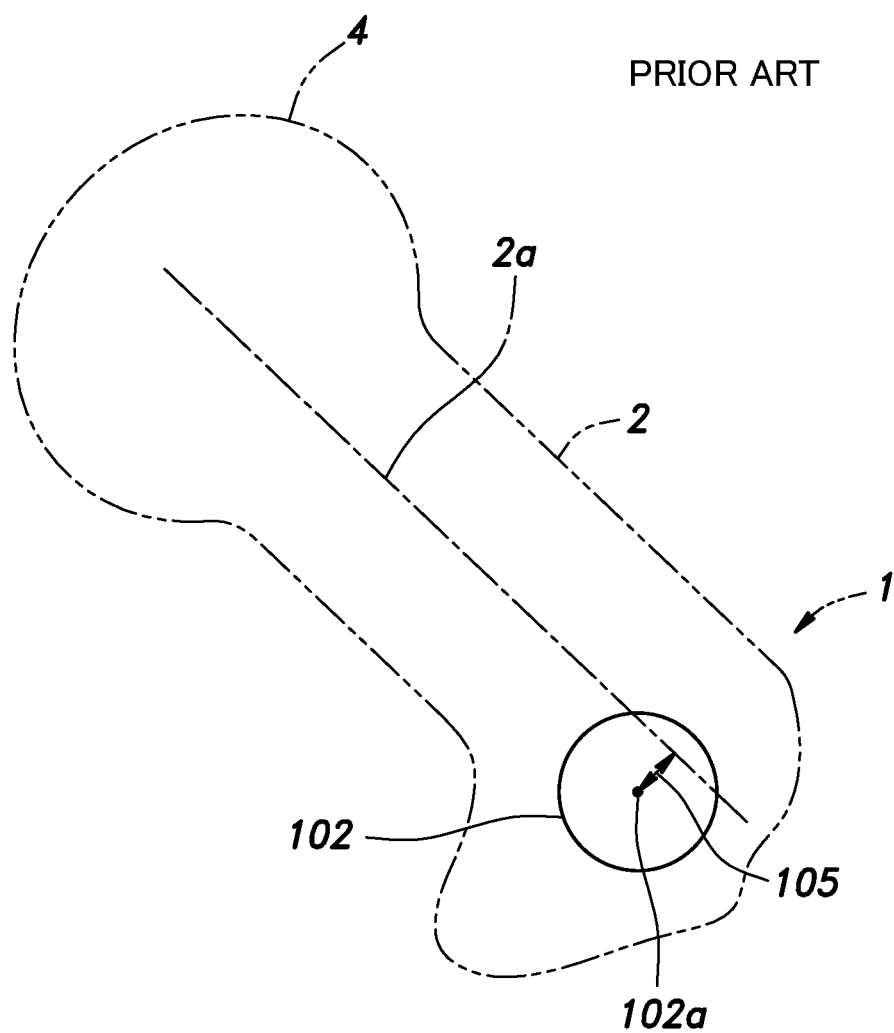
FIG. 5 is a cross sectional view showing a positioning of the conventional intramedullary nail.

The inner fixing member 32 is a linearly extending, rod-like member, and includes a shaft portion 34 configured to be inserted through the through hole 33 and the femoral neck 2 (see FIG. 1), and a front end portion 35 configured to be inserted into the femoral head 4 (see FIG. 1). In this case, the shaft portion 34 and the front end portion 35 are formed by two separate members. The shaft portion 34 and the front end portion 35 may be connected to each other, for instance, by fitting a front end of the shaft portion 34 into a blind hole 36 formed in the rear end of the front end portion 35, or by threading a thread (not shown in the drawings) formed in the front end of the shaft portion 34 into such a blind hole 36 into firm engagement. In the former case, an engagement structure consisting of a groove and a projection fitting into the groove may be provided between the shaft portion 34 and the front end portion 35 so that these two portions may not rotate relative to each other.

The procedure for installing the bone fracture internal fixator 30 is described in the following. First of all, the front end portion 35 is inserted into the femoral head 4 (see FIG. 1), and the intramedullary nail 11 is inserted into the medullary cavity of the femoral shaft 5. Thereafter, the shaft portion 34 is inserted into the through hole 33 with the front end first, and is joined with the front end portion 35.

By making the front end portion 35 separate from the shaft portion 34, when installing the bone fracture internal fixator 30, the need to insert the front end portion 35 through the through hole 33 is eliminated. Therefore, the maximum outer diameter of the front end portion 35 can be made larger than the inner diameter of the through hole 33. By increasing the thickness of the front end portion 35, the fixing force between the front end portion 35 and the femoral head 4 (see FIG. 1) and the resistance to withdrawal increase, and the risk of the femoral head 4 (see FIG. 1) being torn apart can be reduced.

Furthermore, since the front end portion 35 can be made thick without increasing the diameter of the intramedullary nail 31, the diameter of the intramedullary nail 31 can be reduced so that when inserting the intramedullary nail 31 into the femoral shaft 5 (see FIG. 1), the invasiveness of the intramedullary nail 31 to the greater trochanter 6 (see FIG. 1) can be minimized Similarly as in the case of the intramedullary nail 11 of the first embodiment, the intramedullary nail 31 may also be configured so that the central axial line of the through hole 33 is offset from the central axial line of the intramedullary nail 31. Further, as shown in FIG. 12B, instead of offsetting the central axial line of the through hole 33 from the central axial line of the intramedullary nail 31, the central axial line of the front end portion 35 may come close to the central axial line of the femoral neck 2 (see FIG. 1) by bending the shaft portion 34. Further, as shown in FIG. 12C, by shifting (or offsetting) the central axial line of the blind hole 36 for joining the shaft portion 34 to the front end portion 35 from the central axial line of the front end portion 35, the central axial line of the front end portion 35 can be made to come close to the central axial line of the femoral neck 2 (see FIG. 1). These configurations improve the load balance, and allow the pain in the bone fracture 3 to be reduced as compared with the conventional device. Since the repaired part can be subjected to loading from an early stage of recovery, progress of rehabilitation can be accelerated.

Third Embodiment

FIG. 13 shows a bone fracture internal fixator 40 according to a third embodiment. Similarly as in the first and second embodiments, the bone fracture internal fixator 40 includes an intramedullary nail 41 configured to be placed in the medullary cavity of the femoral shaft 5, and a linearly extending, rod-like inner fixing member 42 connecting the femoral head 4 and the femoral shaft 5 to each other. In the bone fracture internal fixator 40 according to the third embodiment, the diameter of the inner fixing member 42 is generally increased, and bone cement, an osteogenic agent, artificial bone or the like can be charged into a part where the inner fixing member 42 is connected to the femoral head 4.

As shown in FIG. 14, the intramedullary nail 41 is formed with a through hole 43 through which the inner fixing member 42 is to be inserted, and the through hole 43 is formed in a widened portion 44 formed in the intramedullary nail 41. In the widened portion 44, the width in the lateral direction orthogonal to the extending direction of the through hole 43 is greater than the upper and lower parts of the intramedullary nail 41. In the illustrated intramedullary nail 41, the central axial line of the through hole 43 intersects with the central axial line of the intramedullary nail 41, but the two central axes may be offset from each other as in the first embodiment. In such a case, the bone fracture internal fixator 40 provides functions and advantages similar to those of the first embodiment. The inner diameter of the through hole 43 is preferably equal to or greater than the width of a part other than the widened portion 44 in the intramedullary nail 41. By providing the widened portion 44, the inner diameter of the through hole 43 can be enlarged, and the inner fixing member 42 can be increased in diameter. As the inner fixing member 42 has a large diameter, the securing force and the withdrawing resistance force that are afforded to the inner fixing member 12 in relation to the femoral head 4 and the femoral shaft 5 can be substantially increased. Furthermore, the load acting between the front end portion 46 of the inner fixing member 42 and the femoral head 4 can be widely distributed.

As shown in FIG. 15, the inner fixing member 42 is a linearly extending, rod-like member, and includes a shaft portion 45 configured to be inserted through the through hole 43 and the femoral neck 2, and a front end portion 46 configured to be inserted into the femoral head 4. The maximum outer diameter of the front end portion 46 is equal to the outer diameter of an intermediate part of the shaft portion 45, and the front end portion 46 and the shaft portion 45 both can pass through the through hole 43. The structures by which the front end portion 46 is secured to the femoral head 4, and the shaft portion 45 is supported by the intramedullary nail 41 are similar to those of the first embodiment.

The shaft portion 45 is provided with a hollow structure internally defining a fluid passage 47, and has a substantially cylindrical shape. An injection hole 48 communicating with the fluid passage 47 is formed on the surface of the front end portion 46. After installing the bone fracture internal fixator 40 in the same manner as in the first embodiment, injectable material 49 such as bone cement, an osteogenic agent, artificial bone or the like may be charged into a space that may be created between the front end portion 46 and the femoral head 4 from an opening 50 formed in the rear end of the shaft portion 45 via the fluid passage 47 and the injection hole 48. The injectable material 49 reinforces the mechanical connection between the front end portion 46 and the femoral head 4, and enlarges the distribution range of the load acting between the front end portion 46 and the femoral head 4. Thereby, the load supporting capability of the front end portion 46 can be increased, and the risk of the femoral head 4 being torn apart by the front end portion 46 can be reduced.

Further, the rear end of the shaft portion 45 is provided with a tapered portion 51 narrowing toward the rear. Since the inner fixing member 42 is increased in outer diameter, the diameter of the bone hole 52 through which the inner fixing member 42 is to be inserted needs to be increased, and the strength of the bone may be lowered. However, by providing the tapered portion 51, the shrinking of the bone hole 52 progresses from an early stage of recovery so that the recovery of the bone strength can be accelerated.

The intramedullary nail 41 is formed with a female threaded hole 53 extending across a lower part thereof, and a lateral screw 54 is threaded into the female threaded hole 53 so as to traverse the lower part of the femoral shaft 5, and to fixedly secure the intramedullary nail 41 to the femoral shaft 5. If desired, a plurality of such female threaded holes 53 and corresponding lateral screws 54 may be provided.

FIGS. 16A-16B show modified embodiments of the front end portion 46. In the modification shown in FIG. 16A, the front end portion 46 is provided with a smooth surface instead of a male threaded portion. In another modified embodiment shown in FIG. 16B, instead of a male threaded portion, a plurality of protrusions 55 are provided on the surface of the front end portion 46 in order to prevent the inner fixing member 42 from turning. The modifications illustrated in FIGS. 16A-16B may also be applied to the first and second embodiments.

In the modification of the third embodiment shown in FIGS. 17A-17B, a structure for preventing the inner fixing member 42 from rotating with respect to the intramedullary nail 41 is added. The shaft portion 45 of the inner fixing member 42 is formed with a groove 56 extending in the extending direction of the through hole 43, or in the axial direction of the shaft portion 45. In addition, the intramedullary nail 41 is provided with a main body 57 in which a through hole 43 is formed, and a projecting member 58 that is fixed to the main body 57 and engaged by the groove 56. A threaded hole 59 extends downward from the upper end of the main body 57, and the threaded hole 59 communicates with the through hole 43. The projecting member 58 has a threaded portion 60 fastened to the threaded hole 59, and a protrusion 61 protruding downward from the threaded portion 60 and engaged by the groove 56.

Component parts of the bone fracture internal fixator 40 other than the projecting member 58 are installed in the femur 1 (see FIG. 1) as in the first embodiment. At this time, the inner fixing member 42 is attached to the femur 1 with the groove 56 facing upward. Thereafter, by rotating the projecting member 58 into the threaded hole 59, and causing the protrusion 61 to be engaged by the groove 56, the rotation of the inner fixing member 42 can be prevented.

This rotation prevention structure can also be applied to the first and second embodiments. When the central axial line of the inner fixing member 42 is offset from the central axial line of the intramedullary nail 41 as in the first embodiment, as shown in FIG. 17C, the projecting member 58 may be formed by combining two separate parts including an upper part 58a formed with a threaded portion 60, and a lower part 58b formed with a protrusion 61 and not formed with a threaded portion such that the protrusion 61 is offset from the central axial line of the lower part 58b.

Fourth Embodiment

FIGS. 18A-18C show a bone fracture internal fixator 70 according to a fourth embodiment. The bone fracture internal fixator 70 includes an intramedullary nail 71 configured to be placed in the medullary cavity of the femoral shaft 5 (see FIG. 1), and a linearly extending, rod-like inner fixing member 72 configured to connect a femoral head 4 (see FIG. 1) and a femoral shaft 5 (see FIG. 1) to each other. The intramedullary nail 71 is provided with a through hole 73, and the inner fixing member 72 is supported by the intramedullary nail 71 by being fitted in the through hole 73 at a rear end part of the shaft portion 74 with a front end portion 75 of the inner fixing member 72 being pierced into the femoral head 4 (see FIG. 1). The fourth embodiment is provided with a structure for preventing the rotation of the inner fixing member 72, and can be applied to any of the structures of the first to third embodiments unless otherwise noted.

As shown in FIG. 18A, the inner fixing member 72 is internally formed with a bore 77 defining an opening 76 at the rear end of the inner fixing member 72. A hole 78 communicating with the bore 77 is formed on the surface of the front end portion 75. After the bone fracture internal fixator 70 is installed in the femur 1 (see FIG. 1) in a similar manner as in the first embodiment, a projecting member 79 is caused to project from the hole 78 via the opening 76 and the bore 77. By engaging the projecting member 79 with the femoral head 4 (see FIG. 1), the rotation of the inner fixing member 72 is prevented.

FIGS. 18B-18C show other means for preventing rotation. The bone fracture internal fixators 70 shown in FIGS. 18B-18C each include an auxiliary screw 80 disposed substantially parallel to the inner fixing member 72. The auxiliary screw 80 is supported by the intramedullary nail 71 by tightly or loosely fitting the rear end side of the auxiliary screw 80 in a second through hole 81 provided in the intramedullary nail 71. A front end portion 82 of the auxiliary screw 80 is formed with a male thread, and is fastened to the femoral head 4 (see FIG. 1). The auxiliary screw 80 may be provided below the inner fixing member 72 as shown in FIG. 18B, or above the inner fixing member 72 as shown in FIG. 18C. Only one such auxiliary screw 80 may be provided for each bone fracture internal fixator 70, but two or more of such auxiliary screws 80 may be provided for each bone fracture internal fixator 70. Since the femoral head 4 and the side of the femoral shaft 5 separated from each other by the bone fracture 3 are fixed to each other by the inner fixing member 72 and the auxiliary screw 80 so that the rotation of the femoral head 4 with respect to the femoral shaft 5 is prevented.

Although the present invention has been described in terms of specific embodiments, the present invention is not limited by such embodiments, and can be modified and substituted in various ways without departing from the spirit of the present invention. For instance, the fluid passage and the injection hole used for injecting injectable material, and the combination of the female threaded hole and the corresponding lateral screw in the third embodiment can also be applied to the first embodiment and the second embodiment. The rotation prevention structure of the third embodiment using a groove and a projection can be modified such that the projection is formed in the inner fixing member and the groove is formed in a part fastened to the main body of the intramedullary nail. The various components of the disclosed embodiments are not necessarily entirely essential for the present invention, but can be omitted and substituted without departing from the spirit of the present invention. For instance, the fluid passage and the injection hole used for injecting injectable material, and the combination of the female threaded hole and the corresponding lateral screw in the third embodiment can be omitted.

Glossary of Terms 10, 30, 40, 70: bone fracture internal fixator
11, 31, 41, 71: intramedullary nail
11a: central axial line of intramedullary nail
12, 32, 42, 72: inner fixing member
13, 33, 43, 73: through hole
13a: central axial line of through hole
14, 44: widened portion
16: curved part
17, 34, 45, 74: shaft portion
18, 35, 46, 75: front end portion
47: fluid passage
48: injection hole
51: tapered part
56: groove
61: projection

The invention claimed is:

1. A bone fracture internal fixator for repairing a bone fracture of a femoral neck, said bone fracture internal fixator comprising:
    an intramedullary nail configured to be passed into a medullary cavity of a femoral shaft and provided with a through hole in an upper part thereof; and
    a rod-shaped inner fixing member including a shaft portion configured to be supported by the intramedullary nail by being fitted into the through hole and to be passed through the femoral neck, and a front end portion configured to be pierced into a femoral head;
    wherein a central axial line of the front end portion of the inner fixing member is offset from a central axial line of the intramedullary nail in a direction configured to be disposed toward a central axial line of the femoral neck when the fixator is implanted in a patient,
    and wherein a lateral dimension of a part of the intramedullary nail defining the through hole, as measured in a direction orthogonal to an extending direction of the through hole, is greater than parts of the intramedullary nail above and below the through hole.

2. The bone fracture internal fixator as defined in claim 1, wherein a rear end part of the shaft portion is narrowed.

3. The bone fracture internal fixator as defined in claim 1, wherein one of the intramedullary nail and the inner fixing member is formed with a groove extending along an extending direction of the through hole, and another of the intramedullary nail and the inner fixing member is formed with a projection engaged by the groove.

4. The bone fracture internal fixator as defined in claim 1, wherein the shaft portion is formed as a tubular member internally defining a fluid passage, and a surface of the front end portion is formed with an injection hole communicating with the fluid passage.

5. The bone fracture internal fixator as defined in claim 1, wherein the intramedullary nail is formed with a female threaded hole extending across a lower part of the intramedullary nail.

6. The bone fracture internal fixator as defined in claim 1, wherein a lower part of the intramedullary nail is provided with a curved part conforming to a shape of an extending direction of a medullary cavity of a femoral shaft.

* * * * *